United States Patent
Crapo et al.

(10) Patent No.: US 8,949,137 B2
(45) Date of Patent: Feb. 3, 2015

(54) MANAGING PATIENT CONSENT IN A MASTER PATIENT INDEX

(75) Inventors: Jared Crapo, Chandler, AZ (US); David M. Coyle, Sandy, UT (US); Carol L. Owen, Sandy, UT (US); Preston Pearson, Salt Lake City, UT (US); Kristen McRae, Salt Lake City, UT (US)

(73) Assignee: Medicity, Inc., Salt Lake City, UT (US)

( * ) Notice: Subject to any disclaimer, the term of this patent is extended or adjusted under 35 U.S.C. 154(b) by 110 days.

(21) Appl. No.: 13/346,721

(22) Filed: Jan. 9, 2012

(65) Prior Publication Data

US 2012/0203571 A1 Aug. 9, 2012

Related U.S. Application Data

(63) Continuation-in-part of application No. 11/416,666, filed on May 2, 2006, now Pat. No. 8,095,386.

(60) Provisional application No. 60/677,754, filed on May 3, 2005.

(51) Int. Cl.
*H04L 29/06* (2006.01)
*G06Q 50/22* (2012.01)
*G06F 19/00* (2011.01)
*G06Q 10/10* (2012.01)

(52) U.S. Cl.
CPC .............. *G06Q 50/22* (2013.01); *G06F 19/322* (2013.01); *G06Q 10/10* (2013.01)
USPC ................................................. 705/3; 726/27

(58) Field of Classification Search
USPC ................................................ 705/3; 726/27
See application file for complete search history.

(56) References Cited

U.S. PATENT DOCUMENTS

| | | | |
|---|---|---|---|
| 7,096,219 B1 * | 8/2006 | Karch | 1/1 |
| 2004/0078238 A1 * | 4/2004 | Thomas et al. | 705/3 |
| 2005/0027567 A1 * | 2/2005 | Taha | 705/2 |
| 2006/0080141 A1 * | 4/2006 | Fusari et al. | 705/2 |
| 2007/0005398 A1 | 1/2007 | Kalyan Toleti et al. | |
| 2007/0083395 A1 | 4/2007 | Fors et al. | |
| 2009/0024417 A1 * | 1/2009 | Marks et al. | 705/3 |
| 2010/0094650 A1 | 4/2010 | Tran et al. | |

OTHER PUBLICATIONS

Ferreira, Anna, et al. "How to break access control in a controlled manner." Computer-Based Medical Systems, 2006. CBMS 2006. 19th IEEE International Symposium on. IEEE, 2006.*
International Search Report from PCT/US13/20673, dated Mar. 18, 2013, 23 pages.

* cited by examiner

*Primary Examiner* — Kambiz Zand
*Assistant Examiner* — Michael Guirguis
(74) *Attorney, Agent, or Firm* — Patent Law Works LLP

(57) ABSTRACT

A system and method for managing patient consent. A data access manager includes a controller, a lookup module, a clinical authorization engine, a logging/auditing unit, a user profile engine, a report module and a user interface engine. The controller manages the core functions and the transmission of data between the data access manager components. The lookup module enables a user to query patient data. The clinical authorization engine authorizes access to patient data. The logging/auditing unit logs and monitors user activity. The user profile engine accesses and updates user profile information. The patient profile engine accesses and updates patient profile information. The report module generates reports related to the user activity. The user interface engine generates user interfaces for displaying the user profiles and patient information data.

20 Claims, 8 Drawing Sheets

Welcome, Administrator

Patient Consent

Submit  Cancel

| PATIENT | DOB | GENDER | SSN |
|---|---|---|---|
| Doe, Jane Smith | 01/01/1950 | F | 999-99-999 |
| 1234 Juniper Ave. | Dover, DE 19901 | | (302) 543-0674 |

Options

◉ Opt-In — 302

○ Opt-Out (default) — 304

Welcome, Sue

Patient Search

4 Records Found

| Last Name | First Name | DOB | Gender | Facility |
|---|---|---|---|---|
| Abc | Angela | 06/21/1962 | Female | Beebe Medical Center |
| Xyz | Angela | 12/08/1966 | Female | Bayhealth Medical Center |
| Mno | Angela | 12/25/1961 | Female | Beebe Medical Center |
| Def | Angela | 07/21/1958 | Female | Beebe Medical Center |

Break Glass

Page 1 of 1    20

321   324   322                                              320

323

MANAGING PATIENT CONSENT IN A MASTER PATIENT INDEX

CROSS-REFERENCE TO RELATED APPLICATIONS

The present application is a continuation-in-part, under 35 USC §120, of U.S. patent application Ser. No. 11/416,666, entitled "System and Method for Using and Maintaining a Master Matching Index," filed May 2, 2006, which claims benefit under 35 USC §119(e) to U.S. Provisional Application No. 60/577,754, entitled "System and Method for Using and Maintaining a Master Matching Index," filed May 3, 2005, the entirety of each of which is hereby incorporated by reference.

BACKGROUND

1. Field of the Invention

The invention relates to managing patient consent. In particular, the invention relates to a system for managing patient consent for accessing patient information in a Master Patient Index.

2. Description of the Related Art

Providing quality health care and related services (e.g., pharmaceutical services, veterinary services) depends on having the ability to reliably access various types of records. In the case of patients, information regarding a particular patient may be needed by various different types of health care related entities. For example, any one a hospital, a health care organization, a clinic or hospital lab, an insurance company, or a pharmacy may need access to particular computerized patient information. Such information retrieval generally occurs by querying a database associated with the health care related entity performing the query. The database typically contains all or part of what is referred to as a "Master Patient Index" (MPI), which is a collection of patient information and identifiers. Particularly, an MPI is a collection of indexed patient records, where each record contains information about a particular patient. In practice, user-level applications submit known or believed patient information to the database, which then uses the MPI to match the incoming data with information stored in the database. If a match is found, the record (or pointer thereto) is returned to the querying entity.

While a typical MPI is designed to work within or for a particular health care related entity (e.g., a single hospital, a medical group), including among disparate information systems across the health care related entity, the increased mobility of individuals throughout the overall health care system and the constant evolution of health care in general requires that patient information be reliably accessible by a local, state, regional or national community of health care related entities.

A problem arises when a physician accesses patient data for a patient that the physician has not yet been assigned. For example, when an emergency room physician treats a patient, the physician needs the patient's medical records without the delay that is incurred when the hospital goes through the normal routines of assigning the patient to the physician. This access to the patient's medical information is referred to as "breaking glass." Once the emergency is addressed, problems arise with whether the physician continues to have access to the medical records, whether there is an opportunity for abusing this system and whether there should be additional protection of patient information for patients that are public figures.

SUMMARY OF THE INVENTION

The technology described in the invention overcomes the deficiencies and limitations of the prior art at least in part by providing a system and method for managing patient consent. The data access manager manages patient consent and user access to patient information. The data access manager receives patient information from a plurality of sources such as a Master Matching Index (MMI), a data retrieval service, healthcare data store, health care related entities, etc. The data access manager determines whether a user requesting the patient information is allowed to access the patient information.

In one embodiment, a MMI includes a collection of patient information and identifiers. An MMI adapter is coupled to the MMI for sending queries to the MMI for a health related entity. The MMI adapter comprises a data access manager that includes a controller, a lookup module, a clinical authorization engine, a logging/auditing unit, a patient profile engine, a user profile engine, a report module and a user interface engine. The controller manages the core functions and the transmission of data between the data access manager components. The lookup module enables a user to query patient data. The clinical authorization engine authorizes access to patient data. The logging/auditing unit logs and monitors user activity. The user profile engine accesses and updates user profile information. The patient profile engine accesses and updates patient profile information. The report module generates reports related to user activity. The user interface engine generates user interfaces for displaying the user profiles, patient profiles and patient data.

BRIEF DESCRIPTION OF THE DRAWINGS

The invention is illustrated by way of example, and not by way of limitation in the figures of the accompanying drawings in which like reference numerals are used to refer to similar elements.

FIG. 3A is a graphical illustration of a user interface for designating patient consent according to one embodiment of the invention.

FIG. 3B is a graphical illustration of a user interface for designating user rights according to one embodiment of the invention.

FIG. 3C is a graphical illustration of a user interface for accessing patient data according to one embodiment of the invention.

DETAILED DESCRIPTION OF THE PREFERRED EMBODIMENTS

Figure 1:
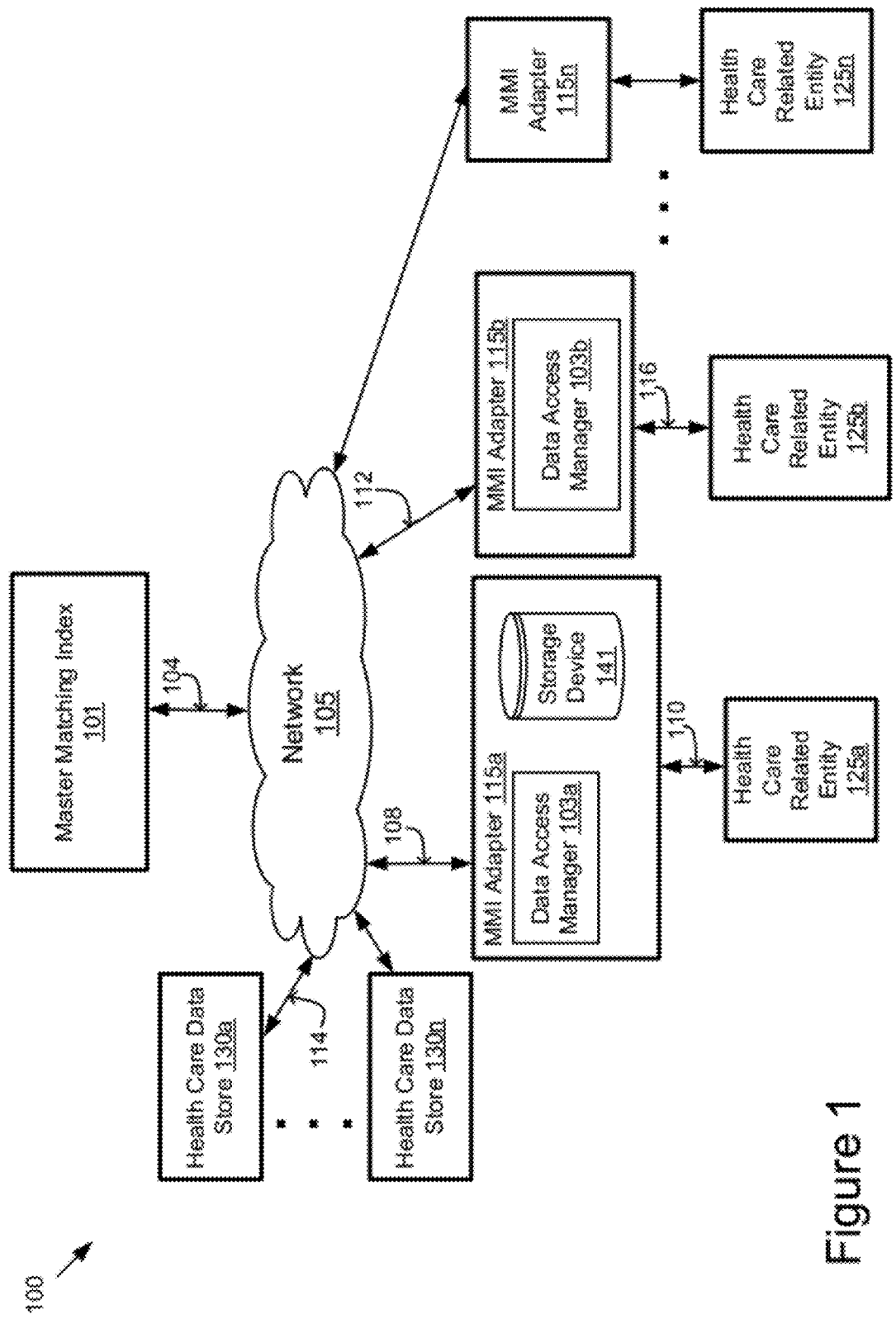
FIG. 1 is a high-level block diagram illustrating a system for managing patient consent according to one embodiment of the invention.

A system and method for managing patient consent are described below. In the following description, for purposes of explanation, numerous specific details are set forth in order to provide a thorough understanding of the invention. It will be apparent, however, to one skilled in the art that the technology described in the various example embodiments can be practiced without these specific details. In other instances, structures and devices are shown in block diagram form in order to avoid obscuring the invention.

Reference in the invention to "one embodiment," "an embodiment" or "an example embodiment" means that a particular feature, structure, or characteristic described in connection with the embodiment is included in at least one embodiment of the description. The appearances of the phrase "in one embodiment" in various places in the invention are not necessarily all referring to the same embodiment.

Embodiments of the present invention generally relate to a Master Matching Index (MMI). An MMI is an index of records or information that may be matched against queries submitted from across a community of entities needing information of the type contained in the MMI. The community of entities coupled to a particular MMI is herein referred to as an MMI-based system or network. In one or more embodiments, an MMI-based network (or system) and method allows different entities to access a central MMI via matching management specific to each of the entities. In other words, an entity in the network may tune its matching algorithm(s) for improved matching accuracy without affecting the matching accuracy of other entities in the network.

It is noted that the scope of the present invention is not limited to matching patient records as is done with an entity-specific Master Patient Index (MPI). Rather, the principles of the present invention are equally applicable to any type of matching index. For example, an MMI in accordance with one or more embodiments may contain patient records as is done with an MPI. In one or more other embodiments, an MMI may contain information relating to physicians. For example, such an MMI may match against name, Drug Enforcement Administration (DEA) number and/or type. Further, in one or more embodiments, an MMI may contain information relating to insurance plans. For example, such an MMI may match against a plan number and/or address for submission of insurance claims. Further, in one or more embodiments, an MMI may contain information relating to pharmacies. For example, such an MMI may match queries against addresses, phone numbers, and/or type. Further, in one or more embodiments, an MMI may contain information relating to veterinary care. For example, such an MMI may match queries against animal records (e.g., state tag number, last known home address). Further, in one or more embodiments, an MMI may contain information relating to product inventory. For example, such an MMI may contain information relating to product weight, cost, type, and/or use. Thus, although one or more embodiments are described below with reference to matching patient records, it is to be understood that any type of MMI may be used similarly, at least with respect to the distributive, matching and process flow aspects described herein.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present embodiment of the invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The invention can take the form of an entirely hardware embodiment, an entirely software embodiment or an embodiment containing both hardware and software elements. In a preferred embodiment, the invention is implemented in software, which includes but is not limited to firmware, resident software, micode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the invention is not described with reference to any particular programming language. It will be appreciated that a variety of programming languages may be used to implement the teachings of the invention as described herein.

System Overview

FIG. 1 illustrates a block diagram of a system 100 for managing patient consent in a Master Patient Index according to one embodiment of the invention. In FIG. 1 and the remaining figures, a letter after a reference number, such as "125a" is a reference to the element having that particular reference number. A reference number in the text without a following letter, such as "125," is a general reference to any or all instances of the element bearing that reference number. In the illustrated embodiment, these entities are communicatively coupled via a network 105.

The illustrated description of a system 100 for managing patient consent includes distributed MMI adapters 115a, 115b . . . 115n that are accessed by health care related entities 125a, 125b . . . 125n, health care data stores 130a . . . 130n and an MMI 101. In the illustrated embodiment, these entities are communicatively coupled via a network 105. The MMI adapters 115a, 115b . . . 115n in FIG. 1 are used by way of example. While FIG. 1 illustrates three MMI adapters 115a, 115b . . . 115n, the description applies to any system architecture having one or more MMI adapters 115n. MMI adapter 115a is coupled to the network 105 via signal line 108. A health care related entity 125a accesses the MMI adapter 115a via signal line 110. MMI adapter 115b is coupled to the network 105 via signal line 112. A health care related entity 125b accesses the MMI adapter 115b via signal line 116.

In one embodiment, the MMI adapter 115a is a hardware server, such as one powered by Medicity®. The MMI adapters 115a, 115b . . . 155n server as interfaces to health care entities 125a, 125b . . . 125n. Those skilled in the art will note that while a distributed MMI adapter 115 and its associated health care related entity 125 may reside on the same system, this need not always be the case. For example, in one or more embodiments, the distributed MMI adapter 115 may be provided as a remote interface to the associated health care related entity 125.

The MMI adapter 115a comprises a data access manager 103a and a storage device 141. The MMI adapter 115b comprises a data access manager 103b and a storage device (not shown). The data access managers 103a, 103b manage patient consent and user access to healthcare information. The storage device 141 stores data managed by the data access manager 103a, such as the identity of users and their patient consent forms.

The health care entities 125 maintain separate systems with their own information and access patient information stored by other entities via the network 105. Health care entities 125 include, but are not limited to, a hospital, a specific department within a hospital (e.g., admissions, laboratory, radiology), a clinic, a physician's office, a pharmacy, a health insurance company, a health care organization (e.g., a Health Maintenance Organization (HMO), a hospital-associated research lab, etc. A health care related entity 125 needing to locate a particular patient record submits a query to the respective MMI adapter 115. The query is embodied in a thread configured by the respective MMI adapter 115 and the thread is transmitted to the MMI 101. Thus, when one of the health care related entities 125 submits a query for a patient record, the query is actually sent as a set of instructions describing how to look for the patient record in the MMI 101.

The MMI 101 includes a collection of patient information. For example, the MMI 101 is a collection of indexed patient records, where each record includes a patient identifier which uniquely identifies a patient and data associated with a patient identifier describing health care information associated with the patient identified by the patient identifier. The MMI 101 is coupled to the network 105 via signal line 104. In one embodiment, the MMI 101 comprises a computing device, such as a server, desktop computer or laptop, including a database having one or more patient identifiers and data associated with a patient identifier describing health care data, such as test results, demographic information, billing information, prescription history or similar data associated with the patient identifier.

In another embodiment, the MMI 101 includes a data retrieval service that fulfills data request and one or more health care data stores 130a . . . 130n that includes health care data associated with the patient identifier. Therefore, the MMI 101 matches data from the data retrieval service with one or more patients, allowing retrieval of health care data associated with a patient from a database stored on the MMI 101 or from a health care data store 130 identified by the MMI 101. Although, the data retrieval service is described as part of the MMI 101, in various embodiments, the MMI 101 and the data retrieval service 107 are on separate servers.

One or more health care data stores 130a . . . 130n communicate with the MMI 101. A health care data store 130a comprises a computing device or other storage device including health care data, such as clinical results, prescription history, insurance or billing information, demographic information or other data associated with providing health care services or products to a patient. For example, health care data store 130a comprises a clinical data catalog including clinical data, a medical insurance database including billing information for one or more patients, a record database including demographic information associated with one or more patients or other store of information applicable to health care services or products provided to one or more patients. Therefore, a health care data store 130a includes health care data associated with one or more patients, allowing retrieval of data associated with a particular patient. The health care data store 130a is coupled to the network 105 via signal line 114. In one embodiment, the health care data storage 130 is stored locally with the health care related entity 125.

The network 105 is a conventional type, wired or wireless, and may have any number of configurations such as a star configuration, token ring configuration or other configurations known to those skilled in the art. Furthermore, the network 105 may comprise a local area network (LAN), a wide area network (WAN) (e.g., the Internet), and/or any other interconnected data path across which multiple devices may communicate. In yet another embodiment, the network 105 may be a peer-to-peer network. The network 105 may also be coupled to or includes portions of a telecommunications network for sending data in a variety of different communication protocols. In yet another embodiment, the network 105 includes Bluetooth communication networks or a cellular communications network for sending and receiving data such as via short messaging service (SMS), multimedia messaging service (MMS), hypertext transfer protocol (HTTP), direct data connection, WAP, email, etc.

Data Access Manager 103

Figure 2:
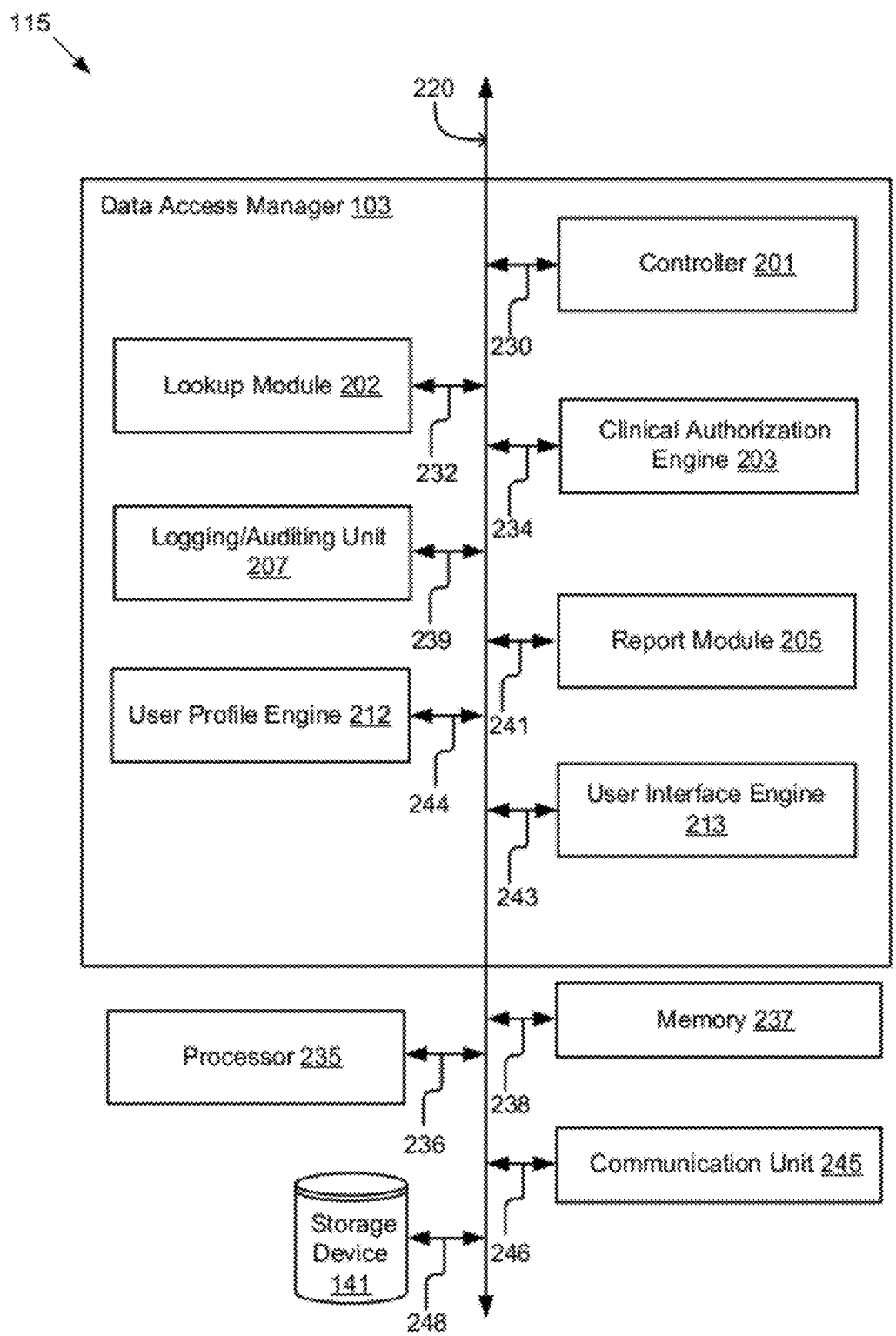
FIG. 2 is a block-diagram of a data access manager according to one embodiment of the invention.

Referring now to FIG. 2, the MMI adapter 115 comprises a data access manager 103, a memory 237, a processor 235, a communication unit 245 and a storage device 141 that are each connected to the bus 220. The bus 220 may represent one or more buses including an industry standard architecture (ISA) bus, a peripheral component interconnect (PCI) bus, a universal serial bus (USB), or some other bus known in the art to provide similar functionality.

The processor 235 comprises an arithmetic logic unit, a microprocessor, a general purpose controller or some other processor array to perform computations and provide electronic display signals to a display device. The processor 235 is coupled to the bus 220 for communication with the other components via signal line 236. Processor 235 processes data signals and may comprise various computing architectures including a complex instruction set computer (CISC) architecture, a reduced instruction set computer (RISC) architecture, or an architecture implementing a combination of instruction sets. Although only a single processor is shown in FIG. 2, multiple processors may be included. The processing capability may be limited to supporting the display of images and the capture and transmission of images. The processing capability might be enough to perform more complex tasks, including various types of feature extraction and sampling. It will be obvious to one skilled in the art that other processors, operating systems, sensors, displays and physical configurations are possible.

The memory 237 stores instructions and/or data that may be executed by processor 235. The memory 237 is coupled to the bus 220 for communication with the other components via signal line 238. The instructions and/or data may comprise code for performing any and/or all of the techniques described herein. The memory 237 may be a dynamic random access memory (DRAM) device, a static random access memory (SRAM) device, flash memory or some other memory device known in the art. In one embodiment, the memory 237 also includes a non-volatile memory or similar permanent storage device and media such as a hard disk drive, a floppy disk drive, a CD-ROM device, a DVD-ROM device, a DVD-RAM device, a DVD-RW device, a flash memory device, or some other mass storage device known in the art for storing information on a more permanent basis.

The communication unit 245 transmits and receives data to and from the MMI 101, health care data stores 130a . . . 130n and other MMI adapters 115. The communication unit 245 is coupled to the bus 220 via signal line 246. In one embodiment, the communication unit 245 includes a port for direct physical connection to the MMI 101 or to another communication channel. For example, the communication unit 245 includes a USB, SD, CAT-5 or similar port for wired communication with the user device 115. In another embodiment, the communication unit 245 includes a wireless transceiver for exchanging data with the MMI 101 or any other communication channel using one or more wireless communication methods, such as IEEE 802.11, IEEE 802.16, BLUETOOTH® or another suitable wireless communication method.

In yet another embodiment, the communication unit 245 includes a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still another embodiment, the communication unit 245 includes a wired port and a wireless transceiver. The communication unit 245 also provides other conventional connections to the network for distribution of files and/or media objects using standard network protocols such as TCP/IP, HTTP, HTTPS and SMTP as will be understood to those skilled in the art.

In one embodiment, the data access manager 103 comprises a controller 201, a lookup module 202, a clinical authorization engine 203, a report module 205, a logging/auditing unit 207, a user profile engine 212 and a user interface engine 213.

The controller 201 is software including routines for managing the core functions of the data access manager 103 and for transmitting data to the different components. In one embodiment, the controller 201 is a set of instructions executable by the processor 235 to provide the functionality below for managing access to data. In another embodiment, the controller 201 is stored in the memory 237 and is accessible and executable by the processor 235. In either embodiment, the controller 201 is adapted for cooperation and communication with the processor 235 and other components of the data access manager 103 via signal line 230.

In one embodiment, the controller 201 performs core functions by listening for data by listening to ports, scanning folders, etc.; inserting data into locations such as a TCP port, folders, etc.; parsing by converting incoming data into objects, such as Java objects; analyzing by examining objects to determine actions; saving data by creating a new topic or adding to a topic that is saved in the storage device 141; formatting by rendering data into the required format, such as by mapping, translating and grouping; sending packages of information for distribution and notifying by, for example, sending an email or a Web alert in response to an event occurring.

The lookup module 202 is software including routines for enabling a user (via a client device) or a third-party application to query data. In one embodiment, the lookup module 202 is a set of instructions executable by the processor 235 to provide the functionality below for receiving a request from a user for patient data, transmitting a query to a MMI 101 or one or more health care data stores 130a . . . 130n and receiving patient data from the MMI 101 or one or more health care data stores 130a . . . 130n. In another embodiment, the lookup module 202 is stored in the memory 237 and is accessible and executable by the processor 235. In either embodiment, the lookup module 202 is adapted for cooperation and communication with the processor 235 and other components of the data access manager 103 via signal line 232.

In one embodiment, the lookup module 202 may be used to transform/translate incoming data from an associated health care related entity to a data format specified or otherwise accurately recognizable by the MMI 101. For example, in a case where the associated health care entity stores dates in month/day/year format and the MMI 101 manages dates in day/month/year format, the lookup module 202 may perform the proper date format conversion between the associated health care related entity and the MMI 101. Further, in another example, information specified with dashes (e.g., insurance identifies, social security numbers) may be converted by the lookup module 202 to a format without dashes (and vice-versa) depending on how data is stored in the MMI 101.

Moreover, the lookup module 202 may be used to resolve competing returned matches. For example, if the MMI 101 is unable to automatically match a patient against records, multiple possible matches may be returned to the lookup module 202, in which case, the lookup module 202 may be used to select one of the returned possible matches. In one or more embodiments, the lookup module 202 may be manually used by a user to resolve a mismatch or multiple returned matches. Further, in one or more embodiments, the lookup module 202 may be configured to automatically resolve a mismatch or multiple returned matches based on some predetermined logic.

Further, the lookup module 202 may be used for the generation of the algorithms/rules for filtering patient data from the MMI 101. This may be accomplished by using performing patient matching with known sample data (representing data from the associated health care related entity). For example, sample data representing 10 known patients may be patient matched, and then, using the lookup module 202, a determination may be made for generating or adjusting algorithms/rules in the lookup module 202 to improve matching accuracy. Thus, in general, such "training" essentially comprises a feedback loop involving feeding sample data and testing patient matching results to adjust the lookup module 202. Further, in one or more embodiments, the sample data may be periodically or regularly changed so as to test different algorithms/rules in the lookup module 202. Further still, in one or more embodiments, the algorithms/rules in the lookup module 202 may be adjusted, whereupon sample data is patient matched to aid in determining which algorithms/rules result in a desired level of patient matching.

The clinical authorization engine 203 is software including routines for authorizing access to and retrieving patient data from the storage device 141 or the master matching index 101. In one embodiment, the clinical authorization engine 203 is a set of instruction executable by the process 235 to provide the functionality below for determining whether a user can access or update patient data. In another embodiment, the clinical authorization engine 203 is stored in the memory 237 and is accessible and executable by the processor 235. In either embodiment, the clinical authorization engine 203 is adapted for cooperation and communication with the processor 235 and other components of the data access manager 103 via signal line 234. The clinical authorization engine 203 supports reading data in one or more formats. For example, the clinical authorization engine 203 supports data formats including Health Level Seven (HL7) and eXtensible Markup Language (XML).

The clinical authorization engine 203 determines whether a user or a third-party application has a right or rights to access a patient data. In one embodiment, the clinical authorization engine 203 receives patient information from the lookup module 202 and analyzes the patient information. The clinical authorization engine 203 analyzes the information by examining an indicator in the information. The indicator indicates whether a patient opted-in to sharing patient information (with or without exceptions) that is associated with the patient or whether the patient opted-out (with or without restrictions). In one embodiment, the indicator is associated with the patient and the indicator applies to all information associated with the patient. For example, the clinical authorization engine 203 receives an indicator that indicates a patient opted-in to sharing the patient's information with other health care entities 125 in the network 105. Therefore, all health care data, such as clinical results, prescription history, insurance or billing information, demographic information or other data associated with providing health care services or products to a patient is accessible to a user that queried the patient. In some embodiments, the physician that generates the health care data controls the indicator. For example, a psychiatrist chooses whether the psychiatrists notes are accessible to other physicians in the system. In some other embodiments, the clinical authorization engine 203 applies state regulations to the opt-in rules regardless of patient consent, such as when a state law prohibits sharing information of minors.

In another embodiment, the indicator is associated with at least a part of clinical data associated with a patient. For example, a patient opted not to share lab work results from the patient's general doctor with a specialist that the patient sees. The clinical authorization engine 203 examines the indicator and determines that the specialist does not have rights to access the lab work results. In yet another embodiment, the indicator is based on the type of data. For example, the type of data may be a pregnancy test for a teen or a Human immunodeficiency virus (HIV) test for a person. In the embodiment, the clinical authorization engine 203 comprises a catalog of data that includes types of data that a user cannot view unless the user has special privileges to view the data.

In yet another embodiment, the clinical authorization engine 203 authorizes access to patient data based on a relationship between the user or a third-party application and the patient. For example, the user is a primary care physician for the patient or a person associated with the physician and the data is lab work for the patient. Therefore, the clinical authorization engine 203 grants access to the lab work because the user has an authorized relationship with the patient. The clinical authorization engine 203 manages authorization based on direct and indirect documentation where a recorded patient consent form is direct and relationships indicated through HL7 transactions are indirect. HL7 transactions normally identify the requesting doctor or organizational component. This information is an indirect consent for the doctor or organizational component to access unrestricted portions of a patient's health record. Given the nature of HIE environments, this may be the primary method of authorizing access to patient information.

In yet another embodiment, the clinical authorization engine 203 denies access to patient data based on a status associated with the patient. For example, Very Important People (VIPs) such as high ranking corporate employees, diplomats, government officials, celebrities, etc. can have a certain status that protects the patient data from being widely distributed. For example, a government official or a celebrity's information is inaccessible because they are public figures. Categories and levels associated with confidential or VIP restrictions on patient data include: business, clinician, individual, low, normal, restricted, very restricted, employee, unwed mother, substance abuse related, HIV related, psychiatry related, sexual and domestic violence related, celebrity, sensitive and taboo.

In one embodiment, the clinical authorization engine 203 gives physicians and staff associated with the provider access to all patient data after the user breaks the glass. In another embodiment, the clinical authorization engine 203 restricts all or part of a patient record if the patient is a VIP or the patient data is marked as being confidential. In another embodiment, the clinical authorization engine 203 restricts access to confidential information to users with the appropriately high security level. A user can request restriction of access to their patient information. For example, the staff cannot access information about a patient's pregnancy test or HIV test if the staff is not associated with the patient or provider. In yet another embodiment, the physicians can see all information for a VIP but the staff is limited from accessing all information. In yet another embodiment, the clinical authorization engine 203 prevents the user from accessing patient information because the time limit for providing access to the patient data has expired.

The clinical authorization engine 203 marks patient data as being associated with a VIP or as confidential in response to receiving a message indicator. The message indicator can be sent in a HL7 segment. Depending upon the type of HL7 segment, all or a portion of the patient data is marked as being confidential. For example, the authorization engine 203 receives an HL7 transaction with a patient data 1 (PD1) segment for flagging the entire patient record with a VIP status and, in response, the authorization engine 203 prevents the patient record from appearing in search results unless the user has security rights to view VIP status or the user is a physician for the patient. The clinical authorization engine 203 does not remove the VIP status unless the request for removal is received from the same source that originally sent the VIP status.

In another example, only a portion of the patient record is marked as having a VIP status when the clinical authorization engine 203 receives an HL7 transaction where the VIP indicator is at the encounter level in a patient visit 2 (PV2) segment or it is sent as a confidential diagnosis in a diagnosis 1 (DG1) segment. A VIP status sent at the encounter level removes everything associated with a specific encounter from view (including orders, results, reports, notes, diagnosis, etc.) unless the user has the security rights to view VIP information or is a physician for the encounter. Everything else in the patient's record remains visible.

In yet another example, an order and not the patient's entire record is marked as having a VIP status when the clinical authorization engine 203 receives a common order segment (ORC). The clinical authorization engine 203 assigns the order and everything associated with the order as confidential and renders the order unsearchable unless the user has security rights to view confidential information or is the physician on the order.

In yet another embodiment, the clinical authorization engine 203 receives a request from a user or a third-party application for emergency access to data that a patient has not consented to sharing. In this embodiment, the user exercises a break glass policy to access patient information. Breaking glass refers to the act of a physician accessing a patient's information when the physician has not yet been assigned to the patient and/or the patient has not given consent to access all or part of the patient's clinical data. As a result, even if the patient opted out of having the patient's data shared among physicians and/or staff, the breaking glass overrides the opt-out option.

For example, in a public health emergency where there is an emergency disease outbreak or a natural disaster, a physician may need access to patient data, such as clinical history, medications, lab work etc. to treat the patient. Alternatively, the physician may need to ignore patient consent and identify effected patients during an emergency, such as a disease outbreak. The clinical authorization engine 203 transmits the requested data during the emergency. In one embodiment, the clinical authorization engine 203 records the reason for breaking glass, including the nature of the emergency and whether the breaking glass was prompted by reporting information to public health officials as required by law. In one embodiment, the breaking glass policy includes an option for automatically giving a group of physicians access to patient information during an emergency, such as a hurricane. This is referred to as a Health Information Exchange (HIE)-wide emergency override. Other breaking glass examples occur when the physician needs the patient's information and it is difficult to request permission, such as when the physician is acting as a consultant for the patient's primary physician.

In one embodiment, the clinical authorization engine 203 grants access to all or part of patient data. In another embodiment, the clinical authorization engine 203 requires at least one of a provider or a physician that accesses the data, an access period and a reason for accessing data from the user. The identity of the requestor can be further identified as an attending, admitting or consulting physician or staff, which is used to associated a nurse or other healthcare provider with a patient. In yet another embodiment, the clinical authorization engine 203 instructs the user interface engine 213 to generate graphical data of a patient consent form that that patient must print and sign before access is granted. The clinical authorization engine 203 transmits information about the location of the physical document to the logging/auditing unit 207, which logs the location as part of the consent authorization documents.

Once the clinical authorization engine 203 grants the user or the third-party application access to the patient data, the clinical authorization engine 203 stores the request and/or the required information in storage device 141 and notifies the lookup module 202 that the patient's data can be present in search results for the period of time that the patient's data is accessible to the user. The user can access the patient data one time, in a limited capacity, is stopped from further accessing the data or at a later time if the time is still in the access period. In one embodiment, the breaking glass policy is only provided to certain users or users associated with certain roles. For example, the physician has access to a policy in an emergency situation. However, regular staff would not be permitted to use the policy.

In some instances, the clinical authorization engine 203 performs anonymizing and de-identifying of the patient data. This data can then be used for clinical trials and other methods without having to be concerned about patient consent because the data is anonymous. In many circumstances, the patients are still notified that their information could be used anonymously so that the patients have informed consent. In another embodiment, the clinical authorization engine 203 also generates an identifier linking the information back to the original patient. The clinical authorization engine 203 can later identify the user through a restricted identification process. In this embodiment, the clinical authorization engine 203 may employ the same restrictions for patient consent and breaking glass that are described above.

The logging/auditing unit 207 is software including routines for logging and monitoring user activity. In one embodiment, the logging/auditing unit 207 is a set of instructions executable by the processor 235 to provide the functionality below for tracking data access. In another embodiment, the logging/auditing unit 207 is stored in the memory 237 and is accessible and executable by the processor 235. In either embodiment, the logging/auditing unit 207 is adapted for cooperation and communication with the processor 235 and other components of the data access manager 103 via signal line 239.

The logging/auditing unit 207 creates a common event log to record each time a user accesses or modifies a patient record or piece of clinical information. For example, the logging/auditing unit 207 tracks when a user changes or adds patient/clinical data. In another example, the logging/auditing unit 207 logs user activity when a user queries/requests patient data or views the patient data. The logging/auditing unit 207 logs the user identifier and context, the event data and time, the event type, the patient identified and context, the encounter context, the data type, the data descriptor and event-specific information. The logging/auditing unit 207 stores the user activity in storage device 141. Those skilled in the art will note that other user activities are recorded by the logging/auditing unit 207. The storage device 141 is coupled to the bus 220 via signal line 248.

In another embodiment, the logging/auditing unit 207 determines inappropriate data access by a user. The logging/auditing unit 207 analyzes data access to determine patterns of inappropriate access by the user. For example, the logging/auditing unit 207 determines that a user broke glass too many times over a predetermined threshold for a period of time. In another embodiment, the logging/auditing unit 207 determines that a user broke glass too many times on certain types of patients. For example, the user broke glass too many times for VIPs, such as celebrities, etc.

The user profile engine 212 is software including routines for accessing user profile information. In one embodiment, the user profile engine 212 is a set of instructions executable by the processor 235 to provide the functionality below for accessing and updating user profiles. In another embodiment, the user profile engine 212 is stored in the memory 237 and is accessible and executable by the processor 235. In either embodiment, the user profile engine 212 is adapted for cooperation and communication with the processor 235 and other components of the data access manager 103 via signal line 244.

The user profile engine 212 registers users. The user profile engine 212 identifies users with a user identifier, classifies users by type and authenticates the users with a password and an optional second factor such as a token-based authentication (e.g. biometric, RFID, etc.). The user profile 212 includes an option for a patient to have access to their information be limited because the patient is a VIP. User names can be assigned by an administrator or self-assigned during a self application or security administrator. If self-assigned, the user profile engine 212 creates the user profile and places it in a work queue for review by the healthcare entity's required process. The user profile engine 212 classifies users by a type that defines a basic set of functional and data type access authorities. Many of these security attributes can be adjusted individually to create users with authority profiles that have been tailored to meet user and environment specific needs. The user profile engine 212 assigns passwords or the user specifies the password.

The user profile engine 212 transmits instructions for the user interface engine 213 to generate graphical data for displaying a user interface to the user for registering the user. The user profile engine 212 then receives user profile information from a user interface engine 213. In the embodiment, the user profile information is for at least one of updating or adding a user profile. The user profile information includes information for allowing or denying access to patient information. For example, the patient can opt-in to having the patient's information exchanged over the network 105 by providing an affirmative authorization by signing a consent form. The patient can also opt-in with restrictions, such as identifying types of information that the patient wants kept confidential. The patient can also opt-out of having the patient's information exchanged over the network 105 by formally requesting that the data not be exchanged. The patient can also opt-out without exceptions, which results in the patient information being exchanged and the consumer being notified through mailings, brochures, posted notices or other means.

The clinical authorization engine 203 retrieves user profile information from the user profile engine 212 by sending a user identifier to the user profile engine 212. In one embodiment, the storage device 141 stores user profile information. The storage device 141 transmits the user profile information to at least one of the clinical authorization engine 203 and the user profile engine 212.

The report module 205 is software including routines for generating reports. In one embodiment, the report module 205 is a set of instructions executable by the processor 235 to provide the functionality below for generating reports. In another embodiment, the patient report module 205 is stored in the memory 237 and is accessible and executable by the processor 235. In either embodiment, the report module 205 is adapted for cooperation and communication with the processor 235 and other components of the data access manager 103 via signal line 241.

The report module 205 generates reports related to user activity. The report module 205 generates a report based on information logged by the logging/auditing unit 207. For example, the report module 205 generates a report that is related to a history of user access to patient information. The report includes instances of breaking glass and information about patient consent including the patient consent documents discussed above with reference to the clinical authorization engine 203. In one embodiment, the report module 205 generates the report for regular review by a security officer and the report is forwarded to peer review or regulatory organizations for action as appropriate. In another embodiment, the report is displayed to an administrator for determining whether inappropriate access by a user occurred. In one embodiment, the report indicates how many times a user broke glass during a period of time. In another embodiment, the report indicates user access to a specific set of patients.

The report module 205 configures the report to include a variety of data including: a user login history, physician logins, patient chart access, patient consent audit transactions, clinical inbox activities, a breaking glass audit log, deliveries, patient merge clinical data repositories, patient move/link MPIs, community document activities, medication history queries and organization or user rights logs. The user login history returns a login history for all users in a specified organization, for a specified user or a number of active users in a specified organization. The physician logins summarizes the annual logins for all physicians in a single repository. The patient chart access provides patient chart access for all users in a specified organization, for a specified patient or for a specified user. The patient consent audit transactions provides audit transactions for a specified organization, for a specified patient or for a specified user. The clinical inbox activity summarizes clinical inbox actions taken by users in a specified organization, summarized which users have taken action on a specified patient's information from the clinical inbox or summarizes which patients have had clinical inbox actions taken by a specified user. The break glass audit log provides a break glass audit log for long and short term uses for all the users in a specified organization, for a specified user or a specified patient, and provides a list of who broke glass for a long or short term to see patients of a specified provider. The delivery report identifies the delivery method and location for each result for a specified organization or for each result for a specified patient. The patient move/link MPI reports returns move and link details by a user or provides a moves and links summary in response to manual input. The community document activity summarizes continuity of care document (CCD) actions taken by users in a specified organization, by which patients have had CCD actions taken by the specified user or by which users have taken action on the specified patient's information using CCDs. The medication history queries summarizes medication history queries initiated by users in a specified organization or by a specified user, and summarizes which users have initiated medication history queries on a specified patient. The organization and user rights log tracks who created or changed organization or user rights as well as which users viewed management reports.

In one embodiment, the report module 205 generates a report for public health officials of instances where a public health emergency occurred. The report contains a list of the people whose information was accessed in addition to any type of patient consent that is part of the record or instances where the physician had to break glass to treat the patient.

Example User Interface Engine

The user interface engine 213 is software including routines for generating graphical data for displaying a user interface. In one embodiment, the user interface engine 213 is a set of instructions executable by the processor 235 to provide the functionality below for generating a user interface. In another embodiment, the user interface engine 213 is stored in the memory 237 and is accessible and executable by the processor 235. In either embodiment, the user interface engine 213 is adapted for cooperation and communication with the processor 235 and other components of the data access manager 103 via signal line 243.

The user interface engine 213 generates a user interface according to instructions received from the clinical authorization engine 203, the report module 205 and the user profile engine 212. In one embodiment, the user interface engine 213 receives consent status from a third-party application. The user opts-in with restrictions and opts-out with exceptions. The restrictions include a time limit, a provider and a data type. The user interface engine 213 is described in more detail below in reference to FIGS. 3A-3D.

Figure 3B:
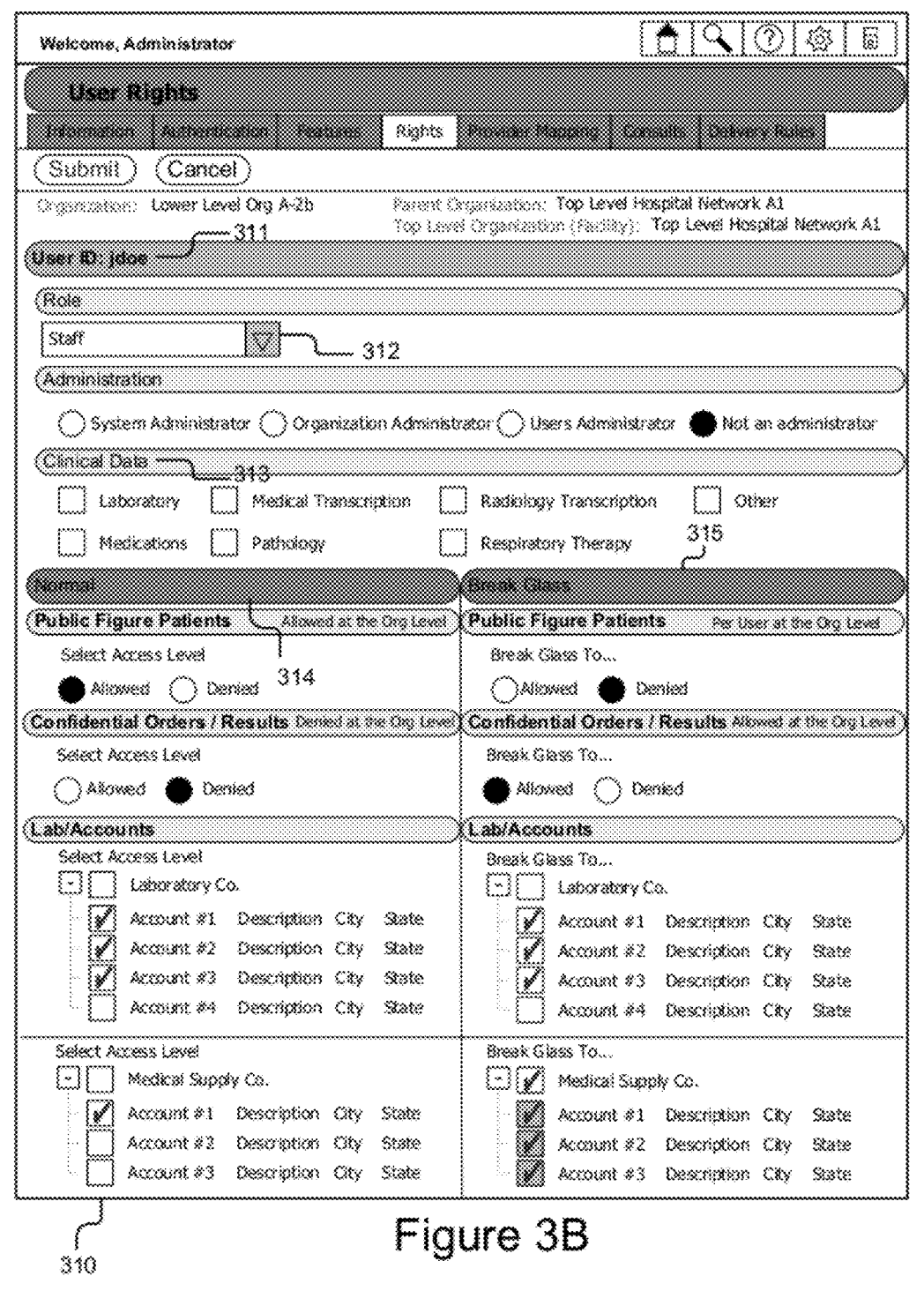

FIG. 3A is a graphic representation 300 of a user interface for designating patient consent. Graphic representation 300 displays patient information and options for designating patient consent. A user or patient designates patient consent by selecting one of a first option 302 to opt-in or a second option 304 to opt-out of sharing clinical data associated with the patient. In one embodiment, a patient does not designate an option to share clinical data and the designation is overridden by a policy of the health care facility 125b that provided service to the patient. In FIG. 3A, the opt-out option 304 is the default policy for opting-out of sharing clinical data associated with the patient FIG. 3B is a graphic representation 310 of a user interface for designating user rights. Graphic representation 310 displays user rights for accessing patient data. The user id 311 indicates that the user rights are for user "jdoe." The user is assigned a role value 312 that sets default values for accessing patient data. In this embodiment, the role value 312 is staff but other options include attending, admitting and consulting physicians. In one embodiment, the default values are overridden by options under user right options 313, 314 and 315.

Options 313 determine whether a user is allowed to access various types of clinical data. For example, a user may be allowed to access lab work, medication history, pathology reports, etc. Options 314 determine whether the user is allowed to access VIP patient data, confidential orders and results and labs or accounts. Options 315 determines whether the user is allowed to access VIP status patient data, confidential orders and results and labs or accounts under an emergency or break glass situation.

FIG. 3C is a graphic representation 320 of a user interface for accessing patient data. Graphical icon 321 indicates that the user viewing the information does not have access to this patient's data and, as a result, would have to click on the graphical icon 321 to view the patient data associated with the line. The user clicks the graphical icon 321 to break glass to view the patient data. The user interface engine 213 receives the request and transmits the request to the clinical authorization engine 203 and the logging/auditing unit 207. The clinical authorization engine 203 determines whether the user is allowed to access the patient data. The logging/auditing unit 207 logs the breaking glass request. If the user is allowed to view the patient data, the user interface engine 213 generates a user interface that includes the patient data.

Graphical icon 322 indicates that a user previously broke glass in order to view patient data associated with patient in that row and the patient data is accessible for a period of time. When the clinical authorization engine 203 receives the request to break glass, the user has the option to create a long term relationship with the patient. Therefore, the user is not required to subsequently break glass to access patient data associated with the patient at a later time.

Graphical icon 323 indicates that the user can break glass for patient search results. This could happen when a user searches for a patient and the results fail to include the patient. By breaking glass on search results, the user can view patient records for patients that exist outside the user's security rights, such as patient records marked as VIP or confidential.

Graphical icon 324 indicates that the patient selected to opt-in with restrictions to having data shared between organizations such that some of the information is inaccessible to the user.

Figure 3D:
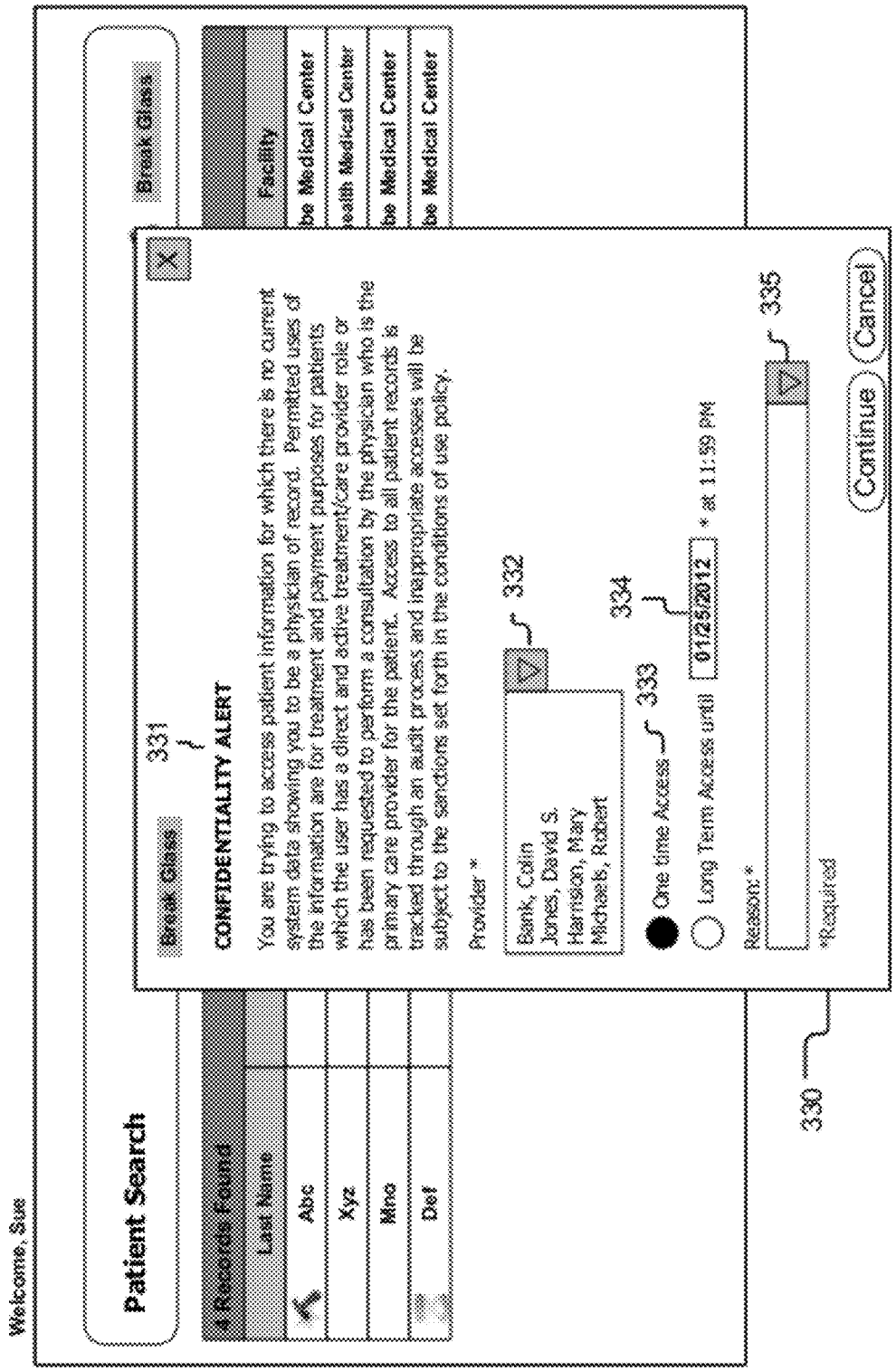
FIG. 3D is a graphical illustration of a user interface for accessing confidential patient information according to one embodiment of the invention.

FIG. 3D is a graphic representation 330 of a user interface for accessing confidential patient records using a break glass policy. Graphic representation 330 displays a confidentiality alert 331 to disclose permitted uses of information and to disclose that the user access is monitored. In the example, the user is required to identify a provider 332 that is treating the patient, an option for the timing of accessing the patient information and a reason 335 for accessing the patient information, such as because the physician is being consulted for a diagnosis. The user selects at least one of a one-time access option 333 and a long-term option 334. The long term option 334 requires a date/time when the access expires.

Methods

Figure 4:
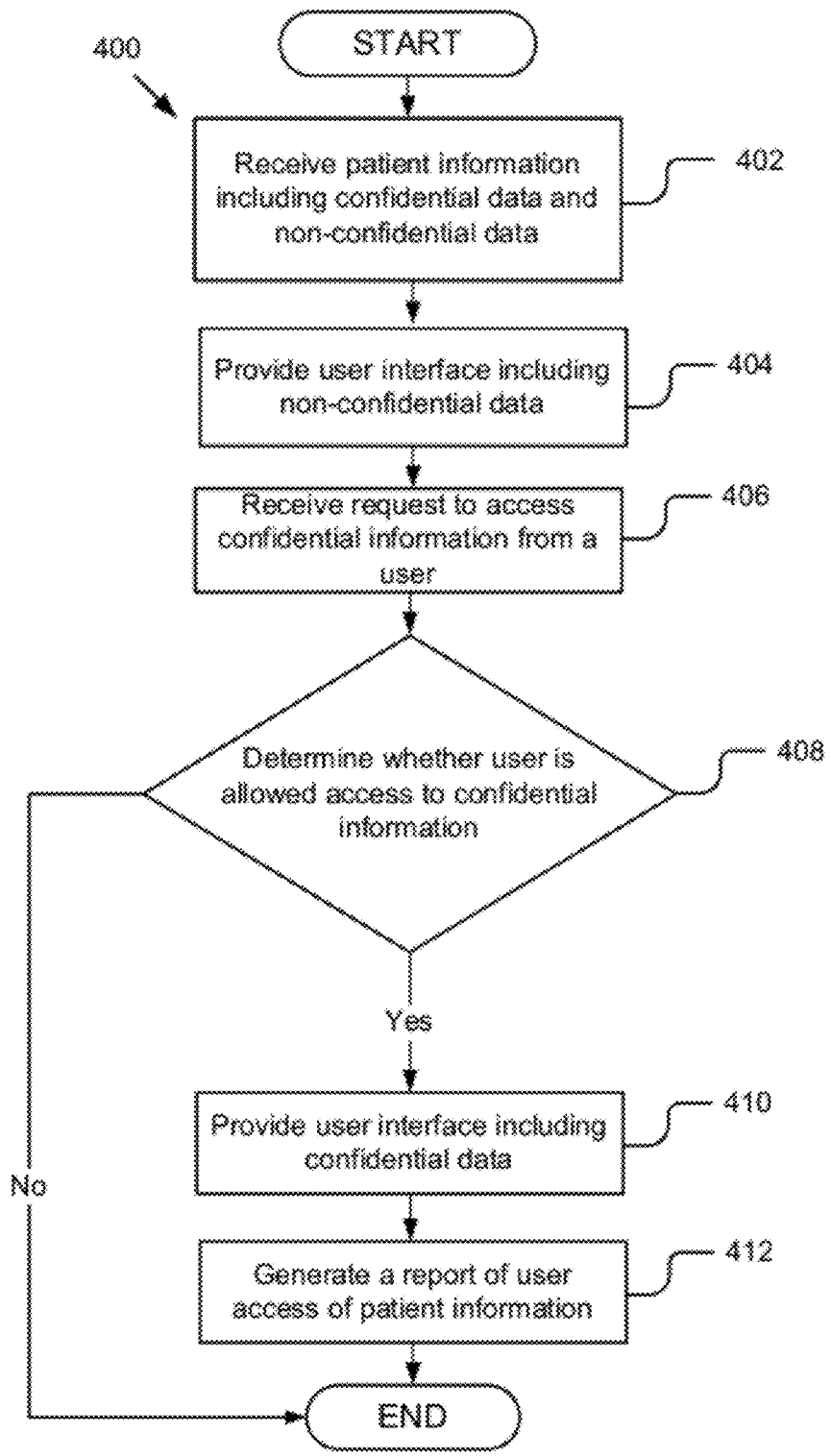
FIG. 4 illustrates a flowchart of a method for managing patient consent according to one embodiment of the invention.
Figure 5:
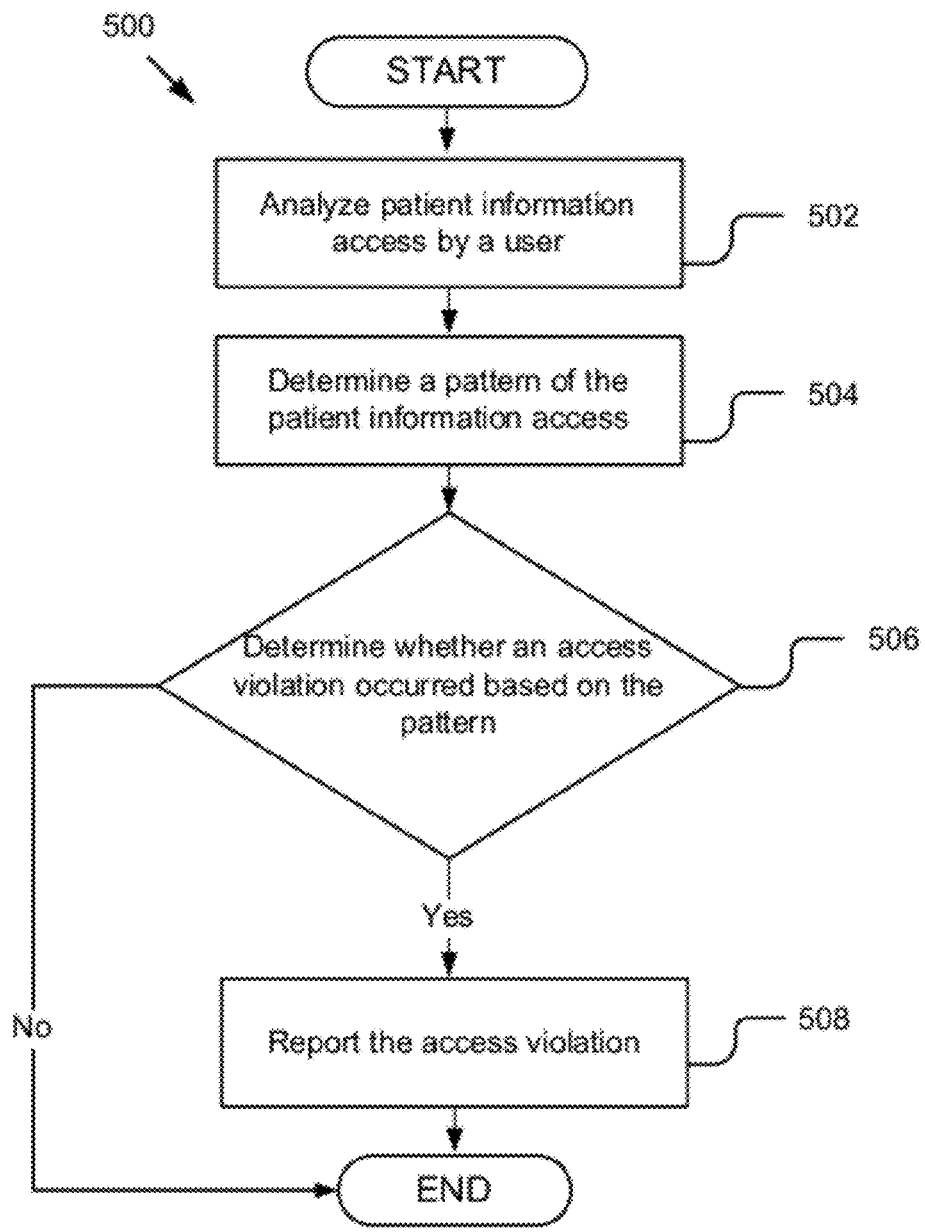
FIG. 5 illustrates a flowchart of a method for monitoring user access to patient information according to one embodiment of the invention.

Referring now to FIGS. 4 and 5, various example embodiments of the invention will be described.

FIG. 4 is a method 400 illustrating one embodiment for managing patient consent. The lookup module 202 queries for a patient information and receives 402 patient information that includes both confidential data and non-confidential data. In one embodiment, the clinical authorization engine 203 determines the confidential data based on indicators in the information. The indicators are associated with at least one of the patient and encounters associated with the patient. In the embodiment, the indicator is a value for opting-out of sharing patient data with disparate health care information systems. In another embodiment, if the patient does not indicate an opt-in or opt-out value, then a default setting of a health care facility 125b that provided patient services/care to the patient is used to determine whether to share or not share data. The health care facility 125b has a policy to opt-in or opt-out by default. A user of a health care entity 125a has access to the data based on at least one of the indicators in the data and a default opt-in/out-out policy of health care entity 125b.

The lookup module 202 instructs the user interface engine 213 to generate a user interface that includes the non-confidential data. Therefore, the lookup module 202 hides the confidential data from the user. The user interface engine 213 provides 404 the user interface to the user. The clinical authorization engine 203 receives 406 a request to access confidential data from the user. In one embodiment, the user requests access using a break glass policy.

The clinical authorization engine 203 determines 408 whether the user is allowed to access to the confidential information. In one embodiment, the clinical authorization engine 203 determines whether the user is allowed to access the confidential information by determining a role that is assigned to the user in a user profile. For example, a user that is assigned a role as a physician is allowed to use the break glass policy. If the user is part of the staff and not a physician, the clinical authorization engine 203 may also request a reason for why the user wants to break glass. Reasons include: providing required medical service, transferring the patient to another facility, receiving a request for consultation, the patient voluntarily seeking medical treatment, providing coverage for the patient's physician, needing information for billing purposes and treating a patient that is in the emergency room. In another embodiment, the clinical authorization engine 203 determines an explicit setting that is associated with the user profile. If the clinical authorization 203 determines that the user is not allowed access, then the method 400 ends. If the clinical authorization 203 determines that the user is allowed access, then the user interface engine 213 generates and provides 410 a user interface including the confidential data. The report module 205 generates 412 a report of user access of patient information.

Now turning to FIG. 5, a method 500 for monitoring user access to patient information is illustrated. The logging/auditing unit 207 logs and analyzes 502 patient information access by one or more users. The logging/auditing unit 207 determines 504 a pattern of the patient information access. The logging/auditing unit 207 determines 506 whether an access violation or inappropriate access occurred based at least in part on the pattern. In one embodiment, the logging/auditing unit 207 monitors how many times a particular user employs the break glass policy over a period of time and determines 506 that the user went over a predetermined threshold. In another embodiment, the user breaks an access threshold based on accessing a type of patient. For example, the user uses the breaks glass policy over the predetermined threshold on VIPs. In one embodiment, the clinical authorization engine 203 applies a machine learning algorithm to the logs to identify suspicious behavior. If the logging/auditing unit 207 determines that there is not an access violation, then the method 500 ends. If the logging/auditing unit 207 determines that there is an access violation, then the logging/auditing unit 207 reports 508 the access violation to an administrator. For example, the logging/auditing unit 207 generates an email or text message that alerts the administrator of the access violation.

The foregoing description of the example embodiments of the invention has been presented for the purposes of illustration and description. It is not intended to be exhaustive or to limit the invention to the precise form disclosed. Many modifications and variations are possible in light of the above teaching. It is intended that the scope of the disclosure be limited not by this detailed description, but rather by the claims of this application. As will be understood by those familiar with the art, the invention may be embodied in other specific forms without departing from the spirit or essential characteristics thereof. Likewise, the particular naming and division of the modules, routines, features, attributes, methodologies and other aspects are not mandatory or significant, and the mechanisms that implement the invention or its features may have different names, divisions and/or formats. Furthermore, as will be apparent to one of ordinary skill in the relevant art, the modules, routines, features, attributes, methodologies and other aspects of the disclosure can be implemented as software, hardware, firmware or any combination of the three. Also, wherever a component, an example of which is a module, of the invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the invention, which is set forth in the following claims.

What is claimed is:

1. A computer-implemented method executed on one or more processors for managing patient consent, the method comprising:
   receiving, with the one or more processors, private patient information associated with a health care information system of a provider;
   determining, with the one or more processors, that the private patient information includes confidential data based on an indicator, wherein data is confidential data when the indicator associated with the data indicates that the data is inaccessible to one or more of another health care information system and another provider, the another health care information system and the another provider having an authorized relationship with the patient;
   receiving a request from a user for accessing the confidential data;
   determining whether the user is allowed to access the confidential data;
   responsive to the user not being allowed to access the confidential data, providing a confidentiality alert to the user;
   analyzing user access of the confidential data;
   determining a pattern of the user access of the confidential data; and
   determining whether an access violation occurred based on the pattern.

2. The method of claim 1, wherein the indicator is associated with at least one of a patient profile and an encounter associated with the patient profile.

3. The method of claim 1, wherein the confidentiality alert requests a type of access and a reason for accessing the confidential data, the reason including an emergency permission.

4. The method of claim 3, further comprising ignoring patient consent to identify affected patients during an emergency.

5. The method of claim 1, further comprising logging access activity by the user.

6. The method of claim 1, wherein multiple users access patient information and further comprising generating a report based on the access of the patient information.

7. The method of claim 1, wherein determining whether the patient information includes confidential data is based on whether a patient opted-in or opted-out of exchanging the patient information.

8. The method of claim 1, further comprising anonymizing the patient information and transmitting the anonymized patient information to the user without patient consent.

9. The method of claim 1, further comprising determining an age of the patient and denying access to the patient information in accordance with a state law.

10. A system for managing patient consent, the system comprising:
one or more processors;
a data access manager stored on a memory and executable by the processor, the data access manager receiving private patient information associated with a health care information system of a provider, determining that the private patient information includes confidential data based on an indicator, wherein data is confidential data when the indicator associated with the data indicates that the data is inaccessible to one or more of another health care information system and another provider, the another health care information system and the another provider having an authorized relationship with the patient, receiving a request from a user for accessing the confidential data and determining whether the user is allowed to access the confidential data;
a user interface engine stored on the memory and executable by the one or more processors, the user interface engine responsive to the user not being allowed to access the confidential data, providing a confidentiality alert to the user; and
a logging unit stored on the memory and executable by the one or more processors, the logging unit analyzing user access of the confidential data, determining a pattern of the user access of the confidential data and determining whether an access violation occurred based on the pattern.

11. The system of claim 10, wherein the indicator is associated with at least one of a patient profile and an encounter associated with the patient profile.

12. The system of claim 10, wherein the confidentiality alert requests a type of access and a reason for accessing the confidential data, the reason including an emergency permission.

13. The system of claim 12, wherein the data access manager ignores patient consent to identify affected patients during an emergency.

14. The system of claim 10, wherein the data access manager logs access activity by the user.

15. The system of claim 10, wherein multiple users access patient information and wherein the data access manager generates a report based on a plurality of access events by the user.

16. The system of claim 10, wherein determining whether the patient information includes confidential data is based on whether a patient opted-in or opted- out of exchanging the patient information.

17. The system of claim 10, wherein the data access manager anonymizes the patient information and transmits the anonymized patient information to the user without patient consent.

18. The system of claim 10, wherein the data access manager determines an age of the patient and denies access to the patient information in accordance with a state law.

19. A computer program product comprising a non-transitory computer useable medium including a computer readable program, wherein the computer readable program when executed on a computer causes the computer to:
receive private patient information associated with a health care information system of a provider;
determine that the private patient information includes confidential data based on an indicator, wherein data is confidential data when the indicator associated with the data indicates that the data is inaccessible to one or more of another health care information system and another provider, the another health care information system and the another provider having an authorized relationship with the patient;
receive a request from a user for accessing the confidential data;
determine whether the user is allowed to access the confidential data;
responsive to the user not being allowed to access the confidential data, provide a confidentiality alert to the user;
analyze user access of the confidential data;
determine a pattern of the user access of the confidential data; and
determine whether an access violation occurred based on the pattern.

20. The computer program product of claim 19, wherein the indicator is associated with at least one of a patient profile and an encounter associated with the patient profile.

* * * * *